United States Patent
Conn

(10) Patent No.: US 9,044,588 B2
(45) Date of Patent: Jun. 2, 2015

(54) REFERENCE ELECTRODE APPARATUS AND METHOD FOR NEUROSTIMULATION IMPLANTS

(75) Inventor: Brian M. Conn, Broomfield, CO (US)

(73) Assignee: Cochlear Limited, Macquarie University, NSW (AU)

( * ) Notice: Subject to any disclaimer, the term of this patent is extended or adjusted under 35 U.S.C. 154(b) by 170 days.

(21) Appl. No.: 12/759,545

(22) Filed: Apr. 13, 2010

(65) Prior Publication Data

US 2010/0268313 A1     Oct. 21, 2010

Related U.S. Application Data

(60) Provisional application No. 61/170,044, filed on Apr. 16, 2009.

(51) Int. Cl.
*A61N 1/00*     (2006.01)
*A61N 1/05*     (2006.01)

(52) U.S. Cl.
CPC ............ *A61N 1/0541* (2013.01); *A61N 1/0558* (2013.01)

(58) Field of Classification Search
CPC ... A61N 1/0541; A61N 1/0558; H04R 25/606
USPC ............ 607/55, 56, 137, 50–52, 136, 139, 25
See application file for complete search history.

(56) References Cited

U.S. PATENT DOCUMENTS 3,918,440 A * 11/1975 Kraus .............................. 602/2
4,532,930 A     8/1985 Crosby et al.
4,809,712 A     3/1989 Kuzma
4,961,434 A    10/1990 Stypulkowski
4,990,845 A     2/1991 Gord
(Continued)

FOREIGN PATENT DOCUMENTS

WO     2008010647 A1     1/2008

OTHER PUBLICATIONS

Loizon, P. C. (Sep. 1998). Mimicking the Human Ear. IEEE Signal Processing Magizine, 101-130.

*Primary Examiner* — Niketa Patel
*Assistant Examiner* — William Levicky
(74) *Attorney, Agent, or Firm* — Lowe Hauptman & Ham, LLP

(57) ABSTRACT

An implantable apparatus and method are provided for use in conjunction with an implantable neurostimulation signal generator that provides an electrical stimulation signal to an active electrode. In auditory stimulation applications, the apparatus includes at least one anchor member having a distal end portion for directly contacting a patient's cranial bone and an electrically conductive portion extending from the distal end portion to a contact location proximal to the distal end portion. An electrical connection line may be electrically interconnected at a first end to the contact location of the anchor member and electrically interconnected at a second end to an implantable auditory neurostimulation signal generator to define a reference electrode. A bracket member may be mounted to a patient's cranial bone utilizing the anchor member, wherein an electrically conductive pathway extends from a first contact location to a second contact location of the bracket member. The first contact location may selectively contact the contact location of the anchor member and the second location of the bracket member may be adapted for electrical interconnection to the electrical connection line.

25 Claims, 6 Drawing Sheets

(56) References Cited

U.S. PATENT DOCUMENTS

| | | |
|---|---|---|
| 5,000,194 A | 3/1991 | van den Honert et al. |
| 5,042,084 A | 8/1991 | Daly |
| 5,443,493 A | 8/1995 | Byers et al. |
| 5,507,303 A | 4/1996 | Kuzma |
| 5,531,774 A | 7/1996 | Schulman et al. |
| 5,571,148 A | 11/1996 | Loeb et al. |
| 5,578,084 A | 11/1996 | Kuzma et al. |
| 5,653,742 A | 8/1997 | Parker et al. |
| 5,667,514 A | 9/1997 | Heller |
| 5,674,264 A | 10/1997 | Carter et al. |
| 5,720,099 A | 2/1998 | Parker et al. |
| 5,755,743 A | 5/1998 | Volz et al. |
| 5,755,747 A | 5/1998 | Daly et al. |
| 5,776,172 A | 7/1998 | Schulman et al. |
| 5,814,095 A * | 9/1998 | Muller et al. .................. 607/57 |
| 5,868,742 A | 2/1999 | Manes et al. |
| 5,876,443 A | 3/1999 | Hochmair et al. |
| 5,897,486 A | 4/1999 | Ball et al. |
| 5,917,346 A | 6/1999 | Gord |
| 5,922,017 A | 7/1999 | Bredberg et al. |
| 5,957,958 A | 9/1999 | Schulman et al. |
| 5,990,845 A | 11/1999 | Sharp et al. |
| 5,999,848 A | 12/1999 | Gord et al. |
| 5,999,849 A | 12/1999 | Gord et al. |
| 5,999,859 A | 12/1999 | Jolly |
| 6,010,532 A | 1/2000 | Kroll et al. |
| 6,035,237 A | 3/2000 | Schulman et al. |
| 6,067,474 A | 5/2000 | Schulman et al. |
| 6,068,652 A | 5/2000 | Cohen et al. |
| 6,070,105 A | 5/2000 | Kuzma |
| 6,074,422 A | 6/2000 | Berrang et al. |
| 6,078,841 A | 6/2000 | Kuzma |
| 6,116,413 A | 9/2000 | Tabor et al. |
| 6,119,044 A | 9/2000 | Kuzma |
| 6,125,302 A | 9/2000 | Kuzma |
| 6,129,753 A | 10/2000 | Kuzma |
| 6,144,883 A | 11/2000 | Kuzma |
| 6,151,400 A | 11/2000 | Seligman |
| 6,157,861 A | 12/2000 | Faltys et al. |
| 6,161,046 A | 12/2000 | Maniglia et al. |
| 6,163,729 A | 12/2000 | Kuzma |
| 6,181,969 B1 | 1/2001 | Gord |
| 6,190,305 B1 | 2/2001 | Ball et al. |
| 6,208,882 B1 | 3/2001 | Lenarz et al. |
| 6,259,951 B1 | 7/2001 | Kuzma et al. |
| 6,266,568 B1 | 7/2001 | Mann et al. |
| 6,272,382 B1 | 8/2001 | Falty's et al. |
| 6,289,246 B1 | 9/2001 | Money |
| 6,289,247 B1 | 9/2001 | Faltys et al. |
| 6,293,903 B1 * | 9/2001 | Kasic et al. .................. 600/25 |
| 6,301,505 B1 | 10/2001 | Money |
| 6,304,787 B1 | 10/2001 | Kuzma et al. |
| 6,308,101 B1 | 10/2001 | Falty's et al. |
| 6,309,410 B1 | 10/2001 | Kuzma et al. |
| 6,321,125 B1 | 11/2001 | Kuzma |
| 6,321,126 B1 | 11/2001 | Kuzma |
| 6,355,064 B1 | 3/2002 | Peeters et al. |
| 6,358,281 B1 | 3/2002 | Berrang et al. |
| 6,374,143 B1 | 4/2002 | Berrang et al. |
| 6,397,110 B1 | 5/2002 | Kuzma |
| 6,411,855 B1 | 6/2002 | Peeters et al. |
| 6,421,569 B1 | 7/2002 | Treaba et al. |
| 6,487,453 B1 | 11/2002 | Kuzma et al. |
| 6,496,734 B1 * | 12/2002 | Money .......................... 607/56 |
| 6,498,954 B1 | 12/2002 | Kuzma et al. |
| 6,549,814 B1 | 4/2003 | Strutz et al. |
| 6,565,503 B2 | 5/2003 | Leysieffer et al. |
| 6,572,531 B2 | 6/2003 | Zilberman et al. |
| 6,592,512 B2 | 7/2003 | Stockert et al. |
| 6,600,955 B1 | 7/2003 | Zierhofer |
| 6,604,283 B1 | 8/2003 | Kuzma |
| 6,620,094 B2 | 9/2003 | Miller |
| 6,629,923 B2 | 10/2003 | Leysieffer |
| 6,697,674 B2 | 2/2004 | Leysieffer |
| 6,757,970 B1 | 7/2004 | Kuzma et al. |
| 6,778,858 B1 | 8/2004 | Peeters |
| 6,807,445 B2 | 10/2004 | Baumann et al. |
| 6,843,870 B1 | 1/2005 | Bluger |
| 6,862,805 B1 | 3/2005 | Kuzma et al. |
| 6,864,755 B2 | 3/2005 | Moore |
| 6,889,087 B2 | 5/2005 | Moore |
| 6,889,094 B1 | 5/2005 | Kuzma et al. |
| 6,922,591 B2 | 7/2005 | Single |
| 6,980,864 B2 | 12/2005 | Faltys et al. |
| 6,996,438 B1 | 2/2006 | Voelkel |
| 7,005,935 B2 | 2/2006 | Moore |
| 7,039,466 B1 | 5/2006 | Harrison et al. |
| 7,047,081 B2 | 5/2006 | Kuzma |
| 7,054,691 B1 | 5/2006 | Kuzma et al. |
| 7,063,708 B2 | 6/2006 | Gibson et al. |
| 7,072,717 B1 | 7/2006 | Wolf et al. |
| 7,076,308 B1 | 7/2006 | Overstreet et al. |
| 7,082,332 B2 | 7/2006 | Blamey et al. |
| 7,085,605 B2 | 8/2006 | Bluger et al. |
| 7,146,227 B2 | 12/2006 | Dadd et al. |
| 7,266,209 B1 | 9/2007 | House |
| 2002/0099421 A1 | 7/2002 | Goldsmith et al. |
| 2004/0133250 A1 | 7/2004 | Ball et al. |
| 2005/0027325 A1 * | 2/2005 | Lahti et al. .................. 607/37 |
| 2005/0187554 A1 * | 8/2005 | Michelson .................. 606/70 |
| 2005/0245971 A1 | 11/2005 | Brockway et al. |
| 2006/0025648 A1 | 2/2006 | Lupin et al. |
| 2006/0058573 A1 | 3/2006 | Neisz et al. |
| 2006/0058819 A1 * | 3/2006 | Kasic et al. .................. 606/151 |
| 2006/0129203 A1 * | 6/2006 | Garabedian et al. ......... 607/45 |
| 2007/0282397 A1 | 12/2007 | Ball et al. |
| 2008/0046035 A1 * | 2/2008 | Fowler et al. .................. 607/55 |
| 2008/0097529 A1 | 4/2008 | Parramon et al. |
| 2008/0140156 A1 | 6/2008 | Rodriguez et al. |

* cited by examiner

REFERENCE ELECTRODE APPARATUS AND METHOD FOR NEUROSTIMULATION IMPLANTS

RELATED APPLICATIONS

This application claims priority to U.S. Provisional Application Ser. No. 61/170,044, filed Apr. 16, 2009, entitled "REFERENCE ELECTRODE APPARATUS AND METHOD FOR NEUROSTIMULATION IMPLANTS", the entirety of which is hereby incorporated by reference.

FIELD OF THE INVENTION

The present invention relates to neurostimulation, and more particularly to a reference electrode apparatus and method for neurostimulation system implants. The invention is particularly apt for auditory neurostimulation applications, and provides an effective and relatively simple approach for defining a reference electrode electrically interconnected to an active electrode stimulation signal generator.

BACKGROUND OF THE INVENTION

The utilization of neurostimulation implant devices is ever-increasing. Such devices typically utilize a plurality of implanted electrodes that are selectively activated to affect a desired neuro-response, including sound sensation, pain/tremor management, and urinary/anal incontinence. By way of primary interest, auditory neurostimulation implant devices include auditory brainstem implant (ABI) and cochlear implant (CI) devices.

In the case of typical CI devices, an active electrode array may be inserted into the cochlea of a patient, e.g. typically into the scala tympani so as to access and follow the spiral curvature of the cochlea. The array electrodes are selectively driven to stimulate the patient's auditory nerve endings to generate sound sensation. In this regard, a CI electrode array works by utilizing the tonotopic organization, or frequency-to-location mapping, of the basilar membrane of the inner ear. In a normal ear, sound vibrations in the air are transduced to physical vibrations of the basilar membrane inside the cochlea. High frequency sounds do not travel very far along the membrane, while lower frequency sounds pass further along. The movement of hair cells, located along the basilar membrane, creates an electrical disturbance, or potential, that can be picked up by auditory nerve endings that generate electrical action pulses that travel along the auditory nerve to the brainstem. In turn, the brain is able to interpret the nerve activity to determine which area of the basilar membrane is resonating, and therefore what sound frequency is being sensed. By directing which electrodes of a CI electrode array are activated, cochlear implants can selectively stimulate different parts of the cochlea and thereby convey different acoustic frequencies corresponding with a given audio input signal.

With typical ABI systems a plurality of active electrodes may be implanted at a location that bypasses the cochlea. More particularly, an array of electrodes may be implanted at the cochlea nucleus, or auditory cortex, at the base of the brain to directly stimulate the brainstem of a patient. Again, the electrode array may be driven in relation to the tonotopic organization of a recipient's auditory cortex to obtain the desired sound sensation.

As may be appreciated, in the case of either ABI electrodes or CI electrodes, audio signals (e.g. from a microphone) may be processed, (e.g. by a speech processor), and utilized to generate stimulation signals utilized to selectively drive the active electrodes for stimulated sound sensation. Further, in both implant approaches, one or more reference electrodes may be interconnected to the source or generator of the active electric stimulation signals. In this regard, it is desirable to provide a consistent, or stable, reference signal to realize optimal signal generation.

SUMMARY OF THE INVENTION

One objective to the present invention is to provide a stable and reliable reference electrode for implantable neurostimulation signal generator applications.

Another objective of the present invention is to provide a reference electrode that is easy to implement in conjunction with implantable neurostimulation systems.

Yet a further objective of the present invention is to provide a reference electrode for use in implantable neurostimulation systems in a manner that is cost effective.

An additional objective of the present invention is to provide a reference electrode for use in implantable neurostimulation systems in a manner that utilizes reduced implant space, and more particularly, that may be utilized free from the positioning of added componentry within the middle ear of a patient.

One or more of the above objectives and additional advantages may be realized by an implantable apparatus that comprises at least one bone contact member having an electrically conductive portion and an electrical interconnection line electrically interconnected or interconnectable thereto.

More particularly for auditory neurostimulation applications, the anchor member(s) may include a distal end portion adapted for directly contacting a patient's cranial bone, and an electrically conductive portion that extends from the distal end portion to a contact location proximal to the distal end portion. In turn, the electrical interconnection line may be electrically interconnected or interconnectable at a first end thereof to the contact location of the anchor member(s) and electrically interconnected or interconnectable at a second end thereof to an implantable auditory neurostimulation signal generator that is connected to one or more active stimulation electrode(s), wherein a reference electrode is defined.

In one aspect, the distal end portion of the anchor member(s) may be adapted for penetration into and securement to a patient's cranial bone. By way of primary example, the anchor member(s) may be defined by a bone screw (e.g. a self-drilling, self-tapping bone screw).

In another aspect, the implantable apparatus may further include a support member, wherein an active electrode may be supportably interconnected to a distal end of the support member. Further, a proximal end portion of the support member may be positioned in fixed relation to a patient's cranial bone (e.g. via an interconnection to the anchor member(s)). In certain embodiments, the support member may include a plastically deformable portion, wherein the plastically deformable portion is deformable (e.g. bendable) to locate and maintain an active electrode in fixed relation to a patient's cochlea.

In an additional aspect, the implantable apparatus may include a bracket member that may be mountable in fixed relation to a patient's cranial bone by the anchor member(s), wherein a proximal end portion of a support member may be selectively interconnected to and supported by the bracket member. By way of example, the bracket member may comprise a central hub portion having a plurality of mounting arms extending outward therefrom in different offset directions. Each of the mounting arms may include one or more apertures for selectively receiving an anchor member(s) therethrough.

In a further aspect, the implantable apparatus may include an interconnection member, interconnected or interconnectable to the bracket member, for selective interconnection of a support member in a desired fixable position relative to the bracket member. In this regard, an interconnection member may be provided to allow for selective angular and/or depth positioning of the support member relative to the bracket member. In one approach, the interconnection member may include a compression member that is selectively compressible about a proximal end portion of the support member, wherein the support member may be slidably advanced retracted relative within a slot of the compression member, and fixedly positioned within the slot upon selective compression by the compression member.

In another aspect, the implantable apparatus may provide for electrical isolation between the defined reference electrode and an active electrode. In this regard, at least one of a support member, a bracket member and an interconnection member may include an electrically non-conductive portion for electrically isolating an active electrode from the reference electrode.

In another aspect, at least a portion of the bracket member may be electrically conductive to define an electrically conductive pathway between a first location and a second location on the bracket member, wherein the first location is electrically interconnectable with the contact location of the anchor member(s). In such arrangements, the electrically conductive pathway of the bracket member comprises a portion of the reference electrode. Further in this regard, the second location of the bracket member may include an electrical lead adaptable to be selectively interconnectable with and disconnectable from a compatible connector end provided at a first end of the electrical connection line. By way of example, compatible male/female connectors may define the electrical lead of the bracket member and connector end of the electrical connection line.

As may be appreciated, the present invention may further comprise a method for providing an implantable reference electrode electrically interconnected to an implantable neurostimulation signal generator that provides an electrical stimulation signal to an active electrode. The method includes directly contacting a distal end portion of at least one anchor member to a patient's cranial bone, wherein an electrically conductive pathway extends from the distal end portion to a contact location located proximal to the distal end portion of the anchor member(s). The method further includes electrically interconnecting the contact location of the anchor member(s) to the implantable auditory neurostimulation signal generator, wherein a reference electrode is defined.

In one aspect, the method may include supporting the active electrode at the distal end of a support member, wherein a proximal end of the support member is interconnectable with the anchor member(s). Additionally, the method may include the step of plastically deforming (e.g. bending) at least a portion of the support member to locate and maintain the active electrode in fixed contact relation with a patient's cochlea.

In a further aspect, the method may include mounting a bracket member in fixed relation to a patient's cranial bone utilizing the anchor member(s). Such mounting step may be completed in overlapping relation with the directly contacting step. For example, in one approach, the anchor member(s) may be defined by a self-tapping, self-drilling bone screw(s), wherein a bone screw may be advanced through an aperture of the bracket member for penetration into and securement to a patient's cranial bone. Correspondingly, the bracket member may be securely mounted in fixed relation to the patient's cranial bone.

In a related aspect, the method may further include interconnecting an interconnection member to the bracket member, and selectively positioning and interconnecting a support member in a desired fixed position relative to the bracket member. By way of example, such selective positioning may provide for positioning of a support member in a desired angular orientation and at desired distance, or depth, relative to the bracket member. Further, a plastically deformable portion of the support member may be plastically deformed, or bent, to facilitate contact positioning of an active electrode into contact with or into an implanted position relative to a patient's cochlea (e.g. at a patient's round window or oval window).

Additional aspects and advantages of the present invention will be apparent to those skilled in the art upon consideration of the further description that follows.

DETAILED DESCRIPTION

Figure 1:
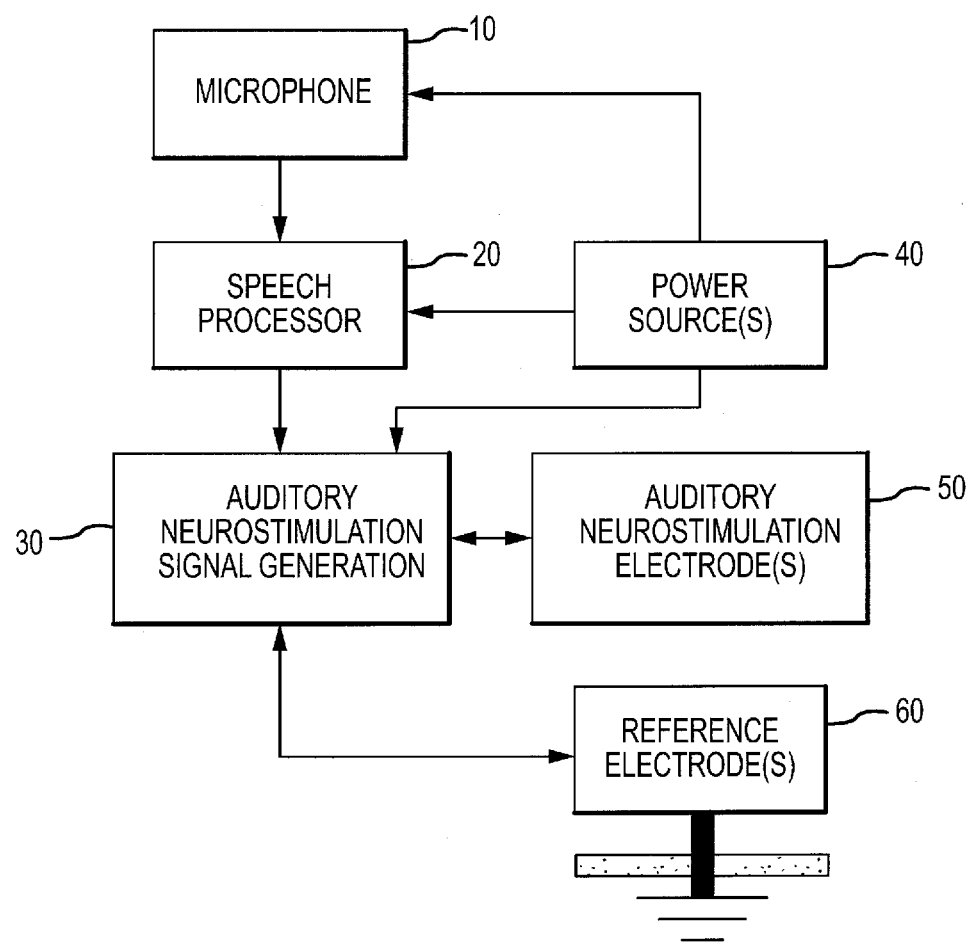
FIG. 1 illustrates an auditory neurostimulation system embodiment comprising the present invention.

FIG. 1 illustrates one auditory neurostimulation system embodiment comprising the present invention. Other neurostimulation applications will be apparent to those skilled in the art.

As shown in FIG. 1, the system may comprise a microphone 10 for receiving an acoustic signal and generating an output audio signal in response thereto. In turn, the system may include a speech processor 20 for processing the audio signal to output a processed audio signal. By way of example, speech processor 20 may scale, phase-shift and/or frequency shape the audio signal in accordance with a programmed processing algorithm to yield the processed audio signal. As may be appreciated, at least certain aspects of such processing maybe established on a patient-specific basis, e.g. to tailor the signal to a given patient's specific audiological needs as determined by a fitting procedure.

As illustrated in FIG. 1, the system 1 may further include an auditory neurostimulation signal generator 30 for receiving the processed audio signal and generating an electrode stimulation signal in response thereto. In this regard, the signal generator 30 may comprise circuit logic and/or processor componentry to utilize the processed audio signal to generate an electrode stimulation signal comprising electrical pulses that may be selectively applied to one or more interconnected implantable auditory neurostimulation electrode(s) 50 for stimulating a patient's auditory system in response. The signal generator may provide the stimulation signal so that the intensity, or magnitude, of the pulses may be selectively established, e.g. current pulses in the range of 0.1 mA to 10 mA may be required for effective stimulation.

In order to power the microphone 10, speech processor 20 and signal generator 30, the system may further comprise one of more interconnected power source(s) 40. By way of example, the power source(s) 40 may comprise a rechargeable battery.

Of note, the system may further include at least one reference electrode 60 anchorable to bone tissue B (e.g. a cranial bone) of a patient and electrically interconnectable with the auditory neurostimulation signal generator 30 to provide a reference signal. As may be appreciated, the bone-anchored return electrode(s) 60 provides a highly consistent and effective signal reference, and may be implemented in a variety of configurations that offer multi-functionality, including for example dual functionality in relation to the positioning of the auditory neurostimulation electrode(s) 50.

In the later regard, reference is now made to FIGS. 2 and 3 which illustrate another auditory neurostimulation system embodiment comprising the present invention. As shown, the system includes at least one active stimulation electrode 140 interconnected to a distal end of a support member 150. In the illustrated embodiment, the active electrode 140 may be of a ball-end configuration, sized for contact interface with a round window or oval window of a patient's cochlea. By way of example, such an arrangement may be employed in applications where high frequency stimulation is required or where tinnitus masking is required. In other embodiments an electrode array may be supportably interconnected to the support member 150, wherein the electrode array comprises a plurality of electrodes supportably mounted on a carrier member adapted for insertion and advancement into a patient's cochlea (e.g. via a patient's oval window or round window).

The stimulation electrode 140 may be electrically interconnectable via a stimulation electrical connection line 152 to a stimulation signal generator that may be housed in an implantable module 200. At least a portion of the stimulation electrical connection line 152 may be of an elongated, flexible construction. The support member 150 may be plastically deformable (e.g. to facilitate selective positioning of the stimulation electrode(s) 140), and supportably interconnectable to a bracket member 160 that may be securable to a patient's cranial bone by one or more anchor member(s) 170 (e.g. bone screws). As will be further described hereinbelow, the anchor member(s) 170 may include a distal end portion adapted for penetration into and securement to a patient's skull.

All or at least a portion of at least one of the anchor member(s) 170 may be electrically conductive, wherein an electrically conductive pathway extends from a distal end portion to a proximal end portion of the anchor member(s) 170. In turn, all or at least a portion of the bracket member 160 may be electrically conductive, wherein an electrically conductive pathway extends between at least a first contact location 162 of bracket member 160 and at least a second contact location 164 of bracket member 160. The first contact location 162 may be provided to contact the distal end portion of an anchor member 170, while the second contact location 162 may be provided to contact a reference electrical connection line 180. As may be appreciated, the electrically conductive portions of the anchor member(s) 170 and bracket 160 combinatively define a reference electrode(s) in the described embodiment.

In one approach, the electrical connection line 180 may be adapted for selective interconnection to a stimulation signal generator that may be housed in an implantable module 200. For example, and as illustrated in FIG. 2, the reference electrical connection line 180 may comprise a flexible elongate portion 182 with a female connector 186 provided at one end and a male connector 184 provided at an opposite end. The female connector 186 may be adapted for selective interconnection to and disconnection from a complimentary male connector provided on the bracket 160 at the above-noted second location 164. In the later regard, a plurality of complimentary male connectors may be provided at a corresponding plurality of second locations 164 spaced about a top end of the bracket 160 to facilitate selective positioning and interconnection of the reference electrical connection line 182 relative to the bracket 160. In another approach, an end of the electrical connection line 180 may be permanently attached to the bracket 160 (e.g. via a weld connection).

Figure 2:
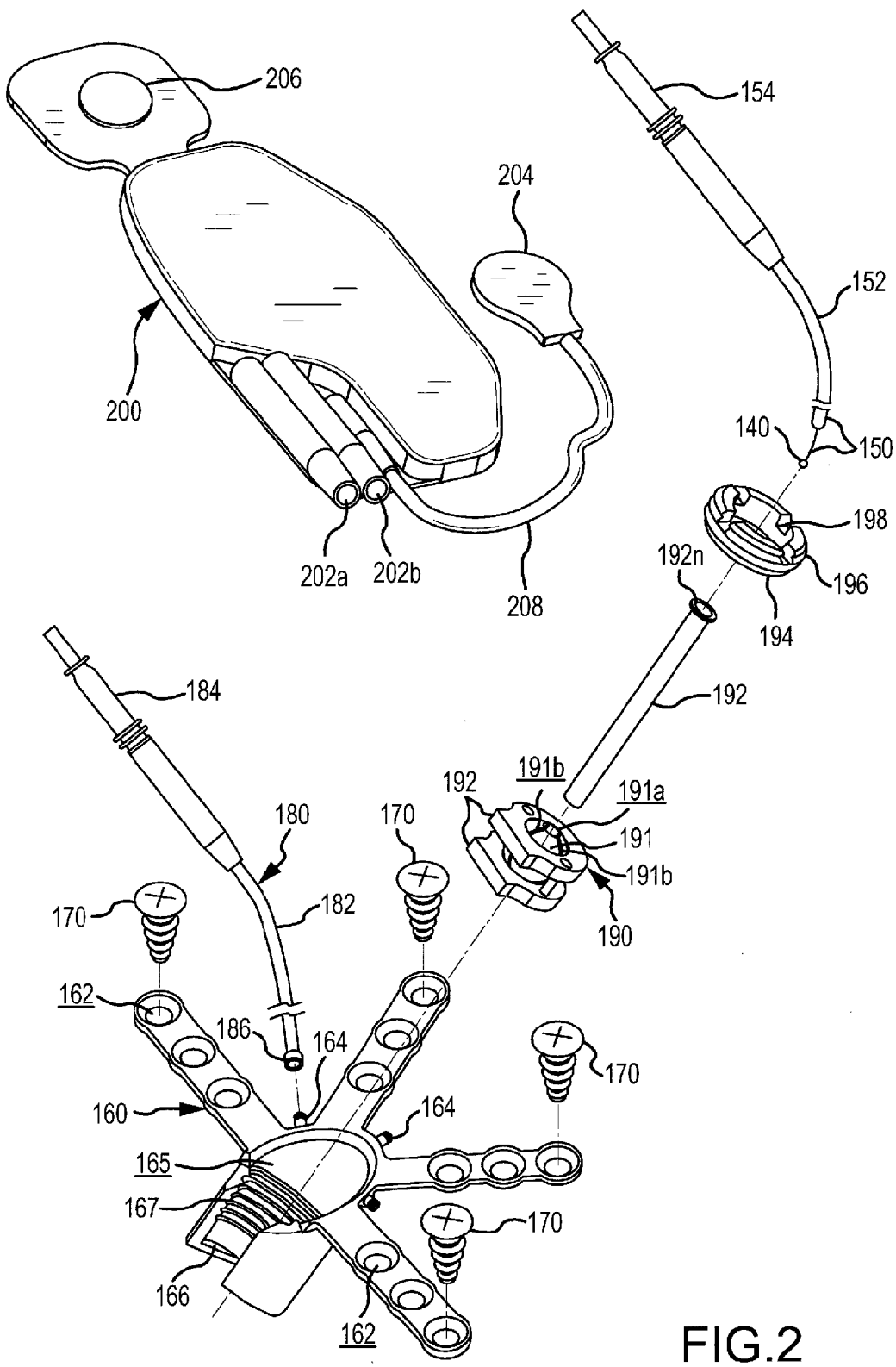
FIG. 2 illustrates another auditory neurostimulation system embodiment comprising the present invention.
Figure 3:
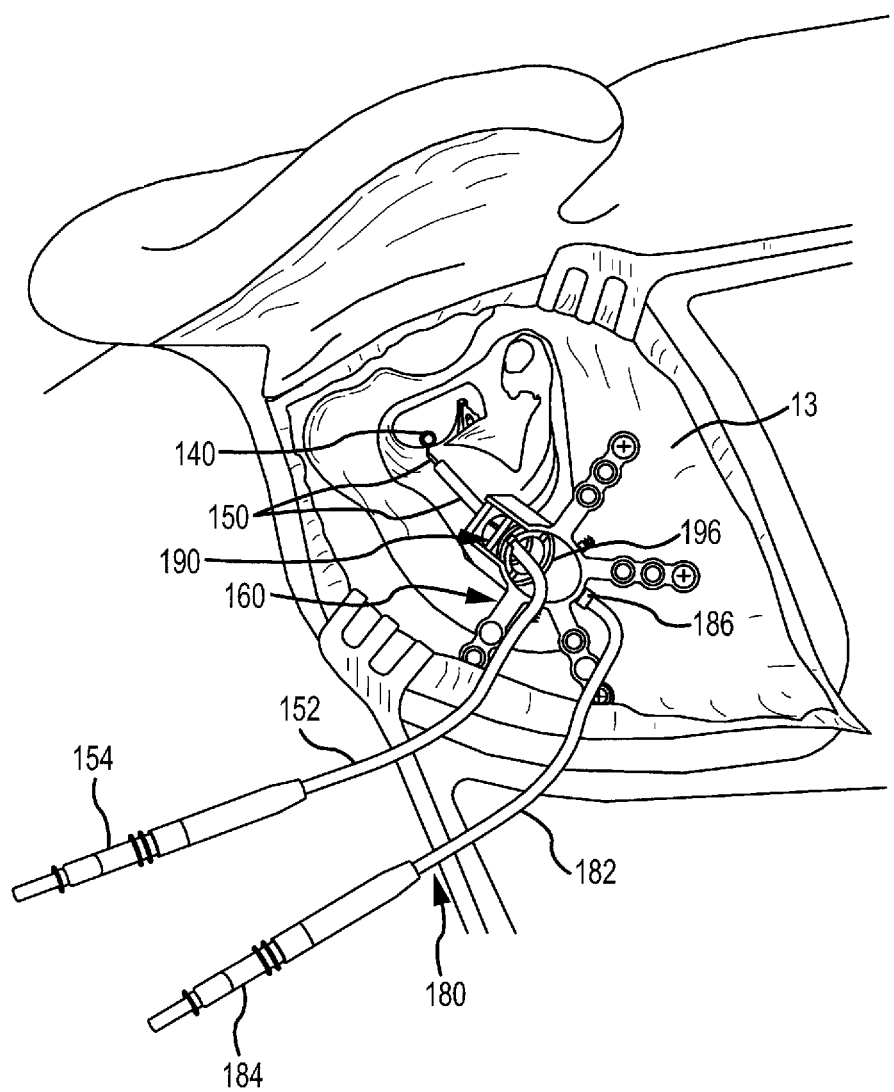
FIG. 3 illustrates the embodiment of FIG. 2 as implanted in a patient.

As shown by FIG. 2, the male connector 184 of the reference electrical interconnection line 180 may be sized for selective insertion into, retention within and disconnection from a first complimentary connector port 202a of the implantable module 200. Similarly, a male connector end 154 interconnected to the stimulation electrical interconnection line 152 may be sized for selective insertion into, retention within and disconnection from a second complimentary port 202b of the implantable housing 200. Such an arrangement facilitates implant positioning of the bracket 160 and implantable module 200 at spaced locations (e.g. in the mastoidectomy and superior and posterior to the mastoidectomy) followed by selective electrical interconnection of the various componentry.

As noted above the implantable housing 200 may comprise a stimulation signal generator. Additionally, the implantable module 200 may include a speech processor for processing an audio output signal received from an implantable microphone 204 that is interconnected to the implantable module 200 via an electrical interconnection line 208. As further illustrated in FIG. 2, a coil member 206 may be disposed within a pendant portion of the implantable module 200. In turn, the coil member 206 may be electrically interconnected to various componentry housed within the implantable housing 200.

In this regard, the coil member 206 may be inductively coupleable with an externally locatable coil member (e.g. located outside of a patient's body) for transcutaneous radio frequency signal transmission therebetween. Such transcutaneous signal may comprise a first signal portion (e.g. a carrier signal portion) for use in recharging a battery power source located within the implantable module 200 and a second portion (e.g. a modulated signal portion) comprising data for use in setting processing parameters for the speech processor housed within the implantable module 200.

With further reference to FIG. 2, the illustrated system may include interconnection componentry for interconnecting the support member 150 to the bracket member 160. By way of example, such interconnection componentry may provide for selective angular positioning and/or depth positioning of a distal end of the support member 150. In this regard, the interconnection componentry may include a swivel member 190 comprising a compressible, rotatable member 191 captured between the opposing plates 192. The swivel member 190 is configured for slideable positioning into a coincidentally configured slot 165, and supportable interface with a flange 166, defined by bracket member 160. The rotatable member 191 may include a central aperture 191a extending therethrough and a plurality of slits 191b extending through an upper portion of the rotatable member 191 to the central aperture 191a.

The interconnection componentry may further include a crimpable tubular member 192 that may be selectively positioned through the central aperture 191a of the rotatable member 191 of the swivel member 190. As shown, the tubular member 192 may comprise a central passageway 192a sized to receive the support member 150 therethrough.

As further illustrated in FIG. 2, the interconnection componentry may also include a lock member 196 having a threaded portion 194 on a first surface and having a tool interface portion 198 located on a second surface. The threaded portion 194 may be provided to threadably interface with a threaded portion 167 provided about a portion of the slot 165 defined by the bracket member 160. More particularly, upon selective threaded, rotatable advancement of the threaded portion 194 of the lock member 196 relative to the threaded portion 167 of the bracket member 160 (e.g. utilizing a tool configured to engage the interface portion 198) the lock member 196 may progressively apply a compressive force to the swivel member 190. In turn, upon compression of the opposing plates 192, the rotatable member 191 may be fixedly located in a desired angular position relative to the bracket member 160 so as to affect a desired angular positioning of the support member 150 and interconnected stimulation electrode 140. Further, upon compression of the opposing plates 192, the slits 191b of the rotatable member 191 may progressively close to apply a compressive force to the tubular member 192. In turn, the tubular member 192 may be crimped to fixedly locate support member 150 and interconnected stimulation electrode 140 at a desired depth location relative to the bracket member 160.

As may be appreciated, the embodiment of FIG. 2 may be utilized to not only define a reference electrode but further to provide for the support and positioning of an active stimulation 140. In this regard, the plastically-deformable portion of the support member 150 may be bent into a desired configuration and the above-described interconnection componentry may be utilized so as to position and maintain the stimulation electrode 140 into a desired contact relationship with a patient's round window or oval window. In turn, a stimulation signal may be provided to the active stimulation electrode 140 from the stimulation signal generator housed in implantable module 200 via the stimulation electrical connection line 152. In this regard, the implantable module 200 may be located in a position that is spaced from the middle ear of a patient (e.g. on the temporal bone) and selectively interconnected to the stimulation electrode 140 via the stimulation electrical interconnection line 152. Similarly, the implantable module 200 may be selectively interconnected to the bracket member 160 via the reference electrical connection line 180, wherein a reference electrode is define by the physically engaged, electrically conductive portions of the anchor member 170 and bracket member 160.

In this regard, to facilitate electrical isolation between the stimulation electrode 140 and the defined reference electrode, the support member 150 may be provided with an outer electrically non-conductive sheath (e.g. compressing as silicone material such as nusil). Additionally, or alternatively, at least a portion of the swivel member 190 (e.g. the rotatable member 191 and/or opposing plates 192) may comprise an electrically non-conductive material, a portion of the tubular member 192 may comprise an electrically non-conductive material and/or a portion of a bracket member 192 may comprise an electrically non-conductive material.

Figure 4:
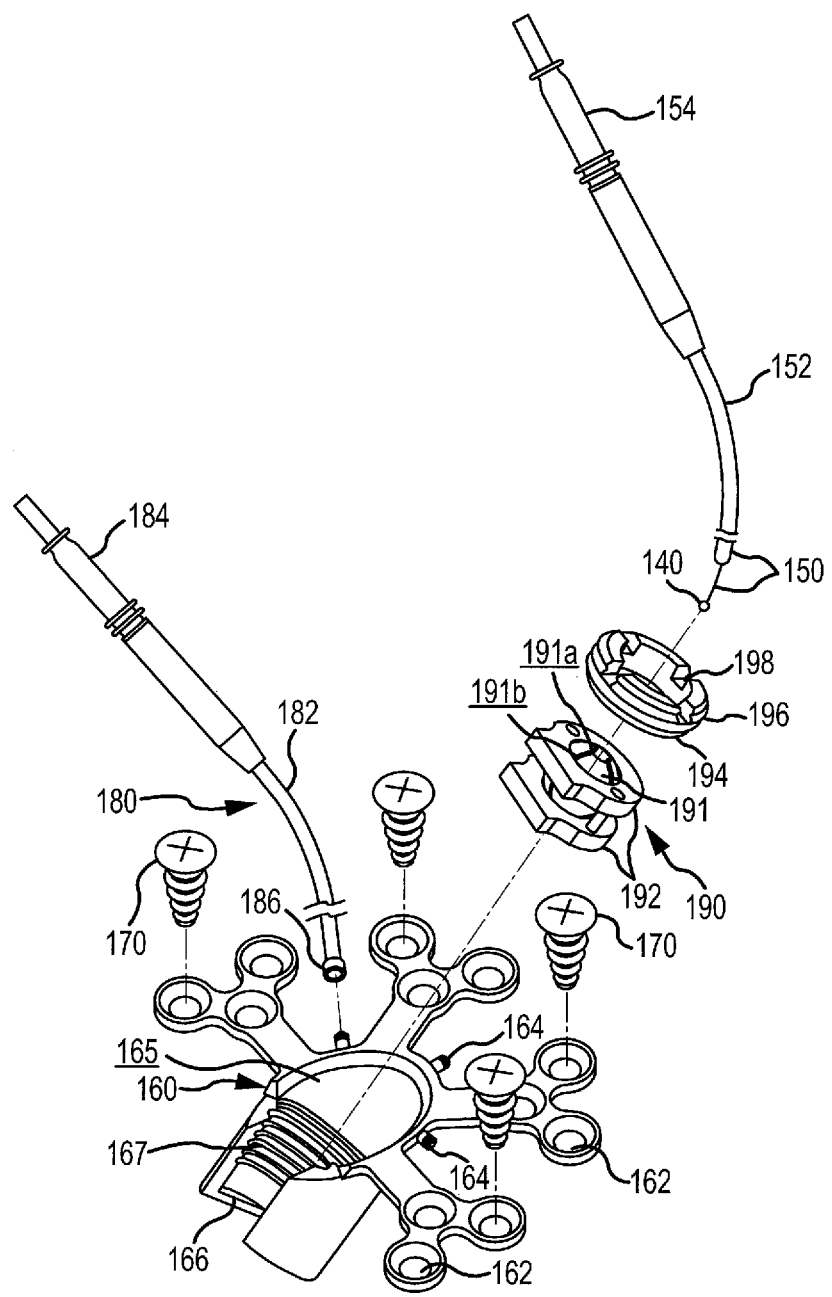
FIG. 4 illustrates another auditory neurostimulation system embodiment comprising the present invention.

Various modifications and extensions to the above-described embodiment would be apparent to those skilled in the art. By way of example, in relation to the embodiment of FIGS. 2 and 3, it may be appreciated that a tubular member 192 thereof may be eliminated. Such an arrangement is shown in FIG. 4. In such arrangement, the aperture 191a through the rotatable member 191 may be sized for receipt of and compressive engagement with support member 150. Other features of the embodiment of FIGS. 2 and 3 may be employed in the embodiment of FIG. 4.

Figure 5:
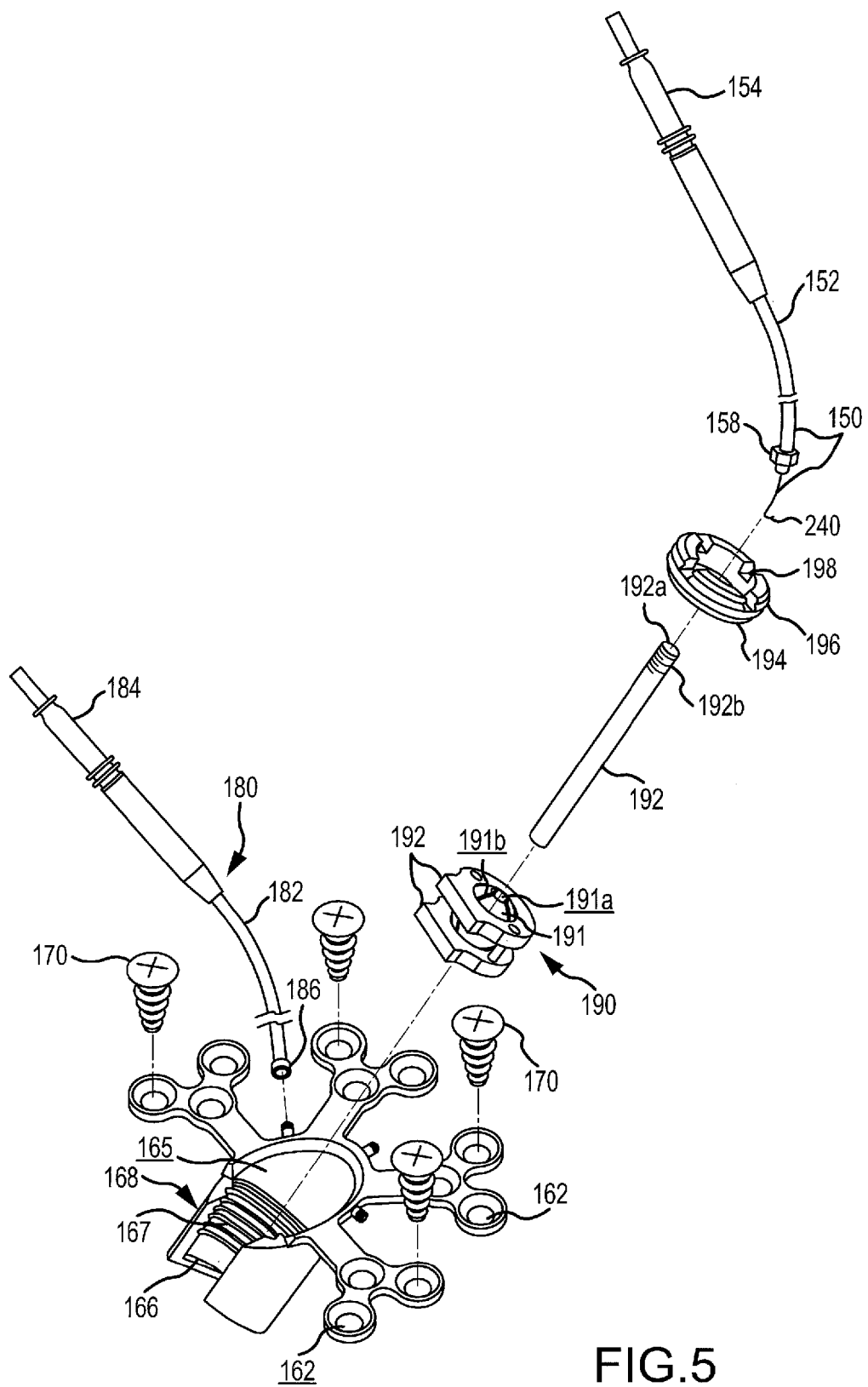
FIG. 5 illustrates an additional auditory neurostimulation system embodiment comprising the present invention.

In a further modified arrangement shown in FIG. 5, a modified stimulation electrode 240 may be employed. More particularly, the active stimulation electrode 240 may comprise an electrode array having a plurality of electrodes mounted on a curved carrier member. The stimulation electrode 240 may be adapted for insertion into and advancement through an incision made in a patient's round window or oval window, wherein electrical pulses may be selectively applied by the electrodes along an internal length of a patient's cochlea.

As further reflected by FIG. 5, the modified embodiment may provide additional features for selective interconnection of the support member 150 to the tubular member 192. In particular, a threaded portion 192b may be provided at one end of the tubular member 192. In turn, a compression coupling member 158 may be slidably disposed about the support member 150. The compression coupling member 158 may comprise internal threads (not shown) adapted for selective rotatable interconnection with the threaded portion 192b of the tubular member 192. In this regard, threaded member 192b may engage member 158 to securely hold the electrode 240 in place. Further, member 192 may be positioned in compression member 191 for finely adjusting the position of electrode 240 and securing the position of electrode 240.

Figure 6:
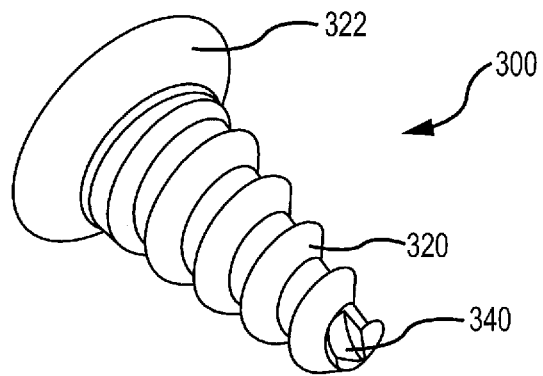
FIGS. 6-8 illustrate various views of a bone screw employable as an anchor member in the various embodiments of the present invention.
Figure 7:
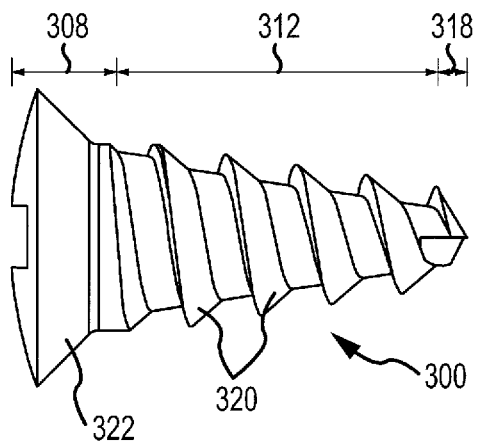
Figure 8:
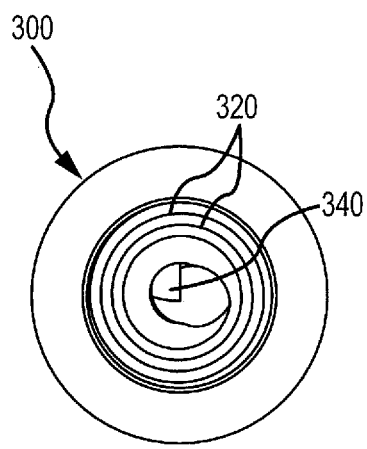

As noted, the various embodiments described above may employ one or more anchor members 170. Reference is now made to FIGS. 6-8, which illustrate various use of a bone screw employable as an anchor member(s) in the described embodiments. In FIG. 7, a side view of a bone screw 300 is shown. Generally, the bone screw 300 comprises three sections: a head section 300, a body section 312 and a tip section 318. Formed along the length of the body region's outside surface and extending from the tip section 318 to the head section 308 is a continuously expanding helical thread 320. Additionally, the tip section 318 of the screw 300 contains a recessed cutting flute 340 that enables the screw 300 to be self-drilling and enables the helical thread 300 to initially "bite" into a bone to allow the screw 300 to be self-tapping. The head section 8 includes a lower flank surface 322 designed to be received within a countersunk recess within a bracket (e.g. bracket 160 in FIG. 2) in order to fasten the bracket to a bone surface.

The screw 300 may be made of any material that provides the desired mechanical properties and is bio-compatible. A mechanical property of particular concern is a material's long term fatigue resistance, as the screws 300 are intended for permanent use and long term fatigue may result in the degradation of the screw 300 over time, necessitating its replacement. Titanium and titanium alloys have been found to be particularly well suited for bio-applications due to their long term fatigue resistance and bio-compatibility. In this regard, the bone screw 300 may be constructed of Grade 6 commercially pure titanium (Ti-6A1-4V E.L.I) or other machinable titanium grades. Additionally, some stainless steels, such as high nickel content stainless steels, may be used as well.

The overall length of the bone screw may be no more than about 4 mm, which coincides with the average minimum thickness of an adult cranial bone. The overall length of the screw 300 actually inserted into a patient's cranial may generally be about 3.5 mm or less.

To provide enhanced gripping force over a short screw geometry, the screw body section 312 is designed having a helical thread 320 that constantly bites into previously undisturbed bone (i.e., creates original bone-to-screw contact) along a majority of the length of the thread 320 as the screw 300 is inserted. In this regard, at least one dimension of the helical thread 320 is expanding along substantially the entire length of the thread 320 between the beginning point of the thread 320 near the tip section 318 to the termination point of the thread 320 near the head section 308. This expansion in at least one dimension ensures that most of the helical thread 320 passes through bone that has not been precut by a previous like-sized portion of the helical thread 320. To allow the thread to expand in at least one dimension, the body section 312 of the screw 300 is generally tapered.

In relation to yet a further modified embodiment of the present invention, a reference electrode may be defined by one or more anchor members 300 having an electrical lead defined thereby or otherwise interconnected therewith, free from inclusion of bracket, interconnection or other support componentry that may be interconnected to an active stimulation electrode.

Figure 9:
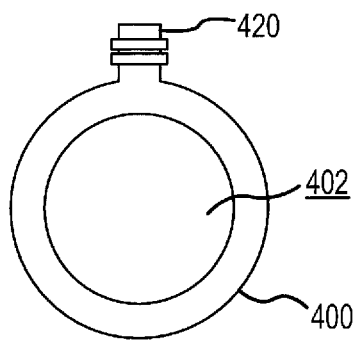
FIG. 9 illustrates an electrical lead member employable with the bone screw embodiment illustrated in FIGS. 6-8.

By way of example, an electrically conductive ring member 400 may be employed as shown in FIG. 9. The ring member 400 may comprise an aperture 402 sized to fit about the anchor member 300 illustrated in FIGS. 6-8, wherein the ring member 400 may be disposed in face to face relation with at least a portion of a lower flank surface located at a proximal end portion of the anchor member(s) 300. In turn, an electrically conductive pathway may be defined between a distal end portion of the anchor member(s), through the ring member 400 to an electrically conductive lead 420 extending from the ring member 400. As may be appreciated, the electrically conductive lead 420 may be configured for selective interconnection to and disconnection from an electrical interconnection line that may be selectively interconnected to a stimulation signal generator as otherwise described hereinabove.

What is claimed is:

1. An implantable apparatus for use with an implantable auditory neurostimulation signal generator that provides an electrical stimulation signal to an active electrode, comprising:
   at least one anchor member, including:
      a distal end portion adapted for directly contacting a patient's cranial bone;
   an electrically conductive portion extending from the distal end portion to a contact location proximal to the distal end portion; and
   an electrical connection line, separate from said at least one anchor member, the electrical connecting line being adapted for electrical interconnection at a first end thereof to said contact location of the at least one anchor member and for electrical interconnection at a second end thereof to said implantable auditory neurostimulation signal generator, wherein upon electrical interconnection of the first end to the contact location and electrical interconnection of the second end to the implantable auditory neurostimulation signal generator, a reference electrode is defined by said implantable apparatus, wherein
   the implantable apparatus further comprises a support member and a bracket member, wherein the support member is configured to supportably interconnect the active electrode to a distal end of the support member, and wherein a proximal end portion of the support member is configured to be positionable in fixed relation to a patient's cranial bone via a swivel member and a lock member supported by the bracket member applying a compressive force on the swivel member.

2. An implantable apparatus as recited in claim 1, wherein said distal end portion of said anchor member is adapted for penetration into and securement to a patient's cranial bone, and further comprising: the bracket member mountable in fixed relation to a patient's cranial bone by said at least one anchor member, wherein said proximal end portion of the support member is selectively interconnectable to said bracket member.

3. An implantable apparatus as recited in claim 2, further comprising: an interconnection member, interconnected or interconnectable to said bracket member for selectively interconnecting the support member in a desired fixed position relative to the bracket member, wherein at least one of said support member, bracket member and interconnection member comprises:
   an electrically non-conductive portion configured to electrically isolate said active electrode and said reference electrode when said support member interconnects said active electrode to the distal end of the support member.

4. An implantable apparatus as recited in claim 2, wherein at least a portion of said bracket member is electrically conductive to define an electrically conductive pathway between a first location and second location of the bracket member, wherein the first location is interconnectable with said contact location of the at least one anchor member, and wherein said electrically conductive pathway of the bracket member comprises a portion of said reference electrode.

5. An implantable apparatus as recited in claim 4, wherein said second location of said bracket member comprises: an electrical lead selectively interconnectable with and disconnectable from a compatible connector provided at said first end of said electrical connection line.

6. An auditory neurostimulation apparatus, comprising:
   the implantable apparatus of claim 1; and
   the implantable auditory neurostimulation signal generator, wherein
   the electrical connection line is electrically interconnected at the first end thereof to said contact location,
   the electrical connection line is electrically interconnected at the second end thereof to said implantable auditory neurostimulation signal generator.

7. An auditory neurostimulation apparatus as recited in claim 6, comprising:
   the active electrode, wherein
   the implantable auditory neurostimulation signal generator is connected to the active electrode.

8. The auditory neurostimulation apparatus as recited in claim 7, wherein:
   an electrically conductive path is present through the electrically conductive portion to the electrical connection line through which current emanating from the active electrode returns to the signal generator.

9. The auditory neurostimulation apparatus as recited in claim 7, wherein:
   the electrically conductive path through the electrically conductive portion to the electrical connection line establishes a path for the reference electrode to function as a signal reference for the implantable auditory neurostimulation signal generator.

10. An implantable apparatus as recited in claim 1, comprising:
    the bracket member secured to the patient's cranial bone via the at least one anchor member, the electrically conductive portion extending through at least a portion of the bracket member; and the active electrode, wherein the active electrode is interconnected to the distal end of the support member, and wherein said support member comprises a plastically deformable portion, said plastically deformable portion being deformable relative to the bracket member to locate and maintain the active electrode in fixed relation to a patient's cochlea.

11. An implantable apparatus as recited in claim 1, wherein:
the at least one anchor member is a separate component from the electrically conductive portion; and
the electrically conductive portion is configured to contact the skull of the recipient.

12. An implantable apparatus as recited in claim 1, wherein:
the electrically conductive portion is part of a bracket member having at least one hole through which the at least one anchor member is fitted, wherein the contact location is spaced away from the at least one hole such that the electrically conductive portion extends from the at least one hole to the contact location.

13. An implantable apparatus for use with an implantable auditory neurostimulation signal generator that provides an electrical stimulation signal to an active electrode, comprising:
an active electrode;
at least one anchor member, including:
a portion adapted for directly contacting a patient's cranial bone;
an electrically conductive portion extending from the portion adapted for directly contacting a patient's cranial bone to a contact location proximal to the portion adapted for directly contacting a patient's cranial bone, wherein the contact location is configured for electrical interconnection with a first end of an electrical connection line, separate from the anchor member, the electrical connection line having a second end provided for electrical connection to the implantable auditory neurostimulation signal generator, wherein upon electrical interconnection of the first end to the contact location and electrical interconnection of the second end to the implantable auditory neurostimulation signal generator, a reference electrode is defined by said implantable apparatus;
a lockable swivel member, wherein the lockable swivel member is configured to enable advancement and rotation of active electrode in an unlocked state of the swivel member; and
a support member and a bracket member, wherein the active electrode is supportably interconnected to a first portion of the support member, and wherein a second portion remote from the first portion of the support member is positionable in fixed relation to a patient's cranial bone and the bracket member via the lockable swivel member in a locked state.

14. An implantable apparatus as recited in claim 13, said support member comprising:
a plastically deformable portion, wherein said plastically deformable portion is deformable to locate and maintain the active electrode in fixed relation to a patient's cochlea.

15. An implantable apparatus as recited in claim 13, wherein said active electrode and said reference electrode are electrically isolated, and wherein said portion adapted for directly contacting a patient's cranial bone of said anchor member is adapted for penetration into and securement to a patient's cranial bone, and further comprising:
the bracket member mountable in fixed relation to a patient's cranial bone by said at least one anchor member, wherein said second portion of the support member is selectively interconnectable to said bracket member.

16. An implantable apparatus as recited in claim 15, further comprising:
an interconnection member, interconnected or interconnectable to said bracket member for selectively interconnecting the support member in a desired fixed position relative to the bracket member,
wherein at least one of said support member, bracket member and interconnection member comprises:
an electrically non-conductive portion electrically isolating said active electrode and said reference electrode.

17. An implantable apparatus as recited in claim 15, further comprising:
an interconnection member, interconnected or interconnectable to said bracket member for selectively interconnecting the support member in a desired fixed position relative to the bracket member,
wherein at least a portion of said bracket member is electrically conductive to define an electrically conductive pathway between a first location and second location of the bracket member, wherein the first location is interconnectable with said contact location of the at least one anchor member, and wherein said electrically conductive pathway of the bracket member comprises a portion of said reference electrode.

18. An implantable apparatus as recited in claim 17, wherein said second location of said bracket member comprises: an electrical lead selectively interconnectable with and disconnectable from a compatible connector provided at said first end of said electrical connection line.

19. An implantable apparatus as recited in claim 13, wherein:
the electrically conductive portion is part of the bracket member having at least one hole through which the at least one anchor member is fitted, wherein the contact location is spaced away from the at least one hole such that the electrically conductive portion extends from the at least one hole to the contact location.

20. A method of providing electrical stimulation to a recipient, comprising:
providing electrical stimulation to tissue of the recipient via delivery of an electrical signal from a stimulation signal generator to an active electrode and via a reference electrode that is in electrical communication with the stimulation signal generator, wherein
the reference electrode comprises at least a portion of an implanted apparatus that includes a fixation element fixed to bone of a recipient and a bracket secured to the bone via the fixation element, and
electrical communication between the reference electrode and the stimulation signal generator takes place along an electrically conductive path that at least in part extends:
from and including at least a portion of the fixation element; and
through at least a portion of the bracket to an electrical connection with a connection line that is in electrical communication with the stimulation signal generator, wherein:
the fixation element is fixed to a cranial bone of the recipient, and thus the implanted component is secured to the cranial bone of the recipient;
the active electrode is located at least one of proximate or inside a cochlea of the recipient; and the conductive path extends from the active electrode to the cranial bone, through at least a portion of the fixation element, through at least a portion of the bracket, to a connection that is in electrical communication with the stimulation signal generator.

21. The method of claim 20, wherein:

the implanted apparatus supports the active electrode in an electrically isolated manner with respect to the reference electrode.

22. The method of claim 20, further comprising:

selecting at least one of a plurality of electrical contacts corresponding to the electrical connection, to which the connection line is to be connected, thereby placing the at least one electrical contacts, and thus the implanted apparatus, into electrical communication with the stimulation signal generator.

23. The method of claim 20, wherein:

the method is executed utilizing a single stimulation generator, and wherein the electrical signal is outputted from the single stimulation generator and results in the provided electrical stimulation that results in a hearing percept via electrical transfer from the active electrode to the reference electrode.

24. The method of claim 20, wherein:

the electrical communication between the reference electrode and the stimulation signal generator establishes a path for the reference electrode to function as a signal reference for the stimulation signal generator.

25. The method of claim 24, wherein:

the electrical signal outputted from the stimulation generator results in the provided electrical stimulation that results in a hearing percept via electrical transfer from the active electrode to the reference electrode.

* * * * *